United States Patent
Moulder et al.

(10) Patent No.: US 8,209,005 B1
(45) Date of Patent: Jun. 26, 2012

(54) SYSTEM AND METHOD FOR REDUCING PAIN IN A HIGH-VOLTAGE LEAD IMPEDANCE CHECK PROCEDURE USING DC VOLTAGE OR CURRENT IN AN IMPLANTABLE MEDICAL DEVICE

(75) Inventors: J. Christopher Moulder, Encino, CA (US); George I. Isaac, Port Hueneme, CA (US); Sergiu Silvian, Los Angeles, CA (US)

(73) Assignee: Pacesetter, Inc., Sylmar, CA (US)

( * ) Notice: Subject to any disclaimer, the term of this patent is extended or adjusted under 35 U.S.C. 154(b) by 1074 days.

(21) Appl. No.: 11/555,183

(22) Filed: Oct. 31, 2006

(51) Int. Cl.
A61B 5/05 (2006.01)
(52) U.S. Cl. .............. 600/547; 607/14; 607/17
(58) Field of Classification Search ............. 600/547; 607/14, 17
See application file for complete search history.

(56) References Cited

U.S. PATENT DOCUMENTS

| | | | |
|---|---|---|---|
| 4,686,988 A | 8/1987 | Sholder | |
| 4,708,142 A | 11/1987 | DeCote, Jr. | |
| 4,712,555 A | 12/1987 | Thornander et al. | |
| 4,729,376 A | 3/1988 | DeCote, Jr. | |
| 4,788,980 A | 12/1988 | Mann et al. | |
| 4,809,697 A | 3/1989 | Causey, III et al. | |
| 4,940,052 A | 7/1990 | Mann et al. | |
| 4,944,298 A | 7/1990 | Sholder | |
| 4,944,299 A | 7/1990 | Silcian | |
| 4,969,467 A | 11/1990 | Callaghan et al. | |
| 5,184,616 A | 2/1993 | Weiss | |
| 5,350,410 A | 9/1994 | Kleks et al. | |
| 5,441,518 A | 8/1995 | Adams et al. | |
| 5,507,781 A | 4/1996 | Kroll et al. | |
| 5,755,742 A | 5/1998 | Schuelke et al. | |
| 5,833,712 A | 11/1998 | Kroll et al. | |
| 6,275,734 B1 | 8/2001 | McClure et al. | |
| 6,311,087 B1 | 10/2001 | Vane et al. | |
| 6,317,628 B1 | 11/2001 | Linder et al. | |
| 6,597,950 B2 | 7/2003 | Linder et al. | |
| 2001/0007056 A1* | 7/2001 | Linder et al. | 600/547 |
| 2003/0088283 A1 | 5/2003 | Ostroff | |

FOREIGN PATENT DOCUMENTS

WO PCT/US00/01674 7/2000

OTHER PUBLICATIONS

Rosen, Michael R., et al.; Cardiac memory and cortical memory; Do learning patterns in neural networks impact on cardiac arrhythmias?; Circulation; Departments of Pharmacology and Pediatrics, Center for Molecular Therapeutics, New York, NY; (c) 2003 American Heart Association.

* cited by examiner

Primary Examiner — Niketa Patel
Assistant Examiner — Michael D Abreu

(57) ABSTRACT

Constant voltage or current is applied to high-voltage leads to determine impedance across medical device leads. Thyristors are used for upper switching components in an H-bridge. Current is sourced into a thyristor's gate from a ground-referenced source. This current then passes from the gate to the cathode and out to the patient. By keeping the current sufficiently low, the thyristors will not conduct from the anode to the cathode. Current passes through the thyristor, lead and patient and is sensed as it returns from the other lead. The sensed current is used to regulate the injected current. Pulses of constant current on the order of tens of milliamperes can be injected and the resulting voltage can be measured. Alternatively, a constant voltage can be applied and the resulting current can be measured to determine lead impedance.

12 Claims, 8 Drawing Sheets

SYSTEM AND METHOD FOR REDUCING PAIN IN A HIGH-VOLTAGE LEAD IMPEDANCE CHECK PROCEDURE USING DC VOLTAGE OR CURRENT IN AN IMPLANTABLE MEDICAL DEVICE

BACKGROUND OF THE INVENTION

1. Field of the Invention

The present invention is related to high-voltage lead impedance checks in implanted medical devices, as well as circuitry used in the devices.

2. Background Art

It is of critical importance in an implantable medical device ("IMD") that appropriate high-voltage lead impedance ("HVLI") be monitored. Too high of an impedance indicates that there may be a problem with lead integrity or placement and revision surgery may be indicated. Methods in use today are not painless and can be felt by the patient. An HVLI check ("HVLIC") must be performed periodically to ensure lead integrity, causing discomfort and increased stress of the patient.

Therefore, what is needed is a method and apparatus for reducing or eliminating pain caused by HVLIC.

BRIEF SUMMARY OF THE INVENTION

Constant voltage or current injected through high-voltage leads of the IMD can be used to determine the impedance. This is made possible through the use of thyristors, such as triacs or silicone controlled rectifiers ("SCRs") for the upper switching components in an H-bridge. Current (or voltage) may be applied to the gate of the thyristor from a ground-referenced source. This current then passes from the gate to the cathode and out to the patient. By keeping the current sufficiently low, the thyristors will not conduct from the anode to the cathode.

Current enters the gate and passes through the thyristor, lead, and patient, and is sensed as it returns to the other lead. The sensed current is used to regulate the injected current in the constant current method. Pulses of constant current on the order of tens of milliamperes can be injected and the resulting voltage can be measured. Alternatively, constant voltage can be applied and the resulting current can be measured to determine lead impedance. The voltage induced across the patient would be, at most, comparable to a pacing pulse.

Further embodiments, features, and advantages of the present invention, as well as the structure and operation of the various embodiments of the present invention, are described in detail below with reference to the accompanying drawings.

BRIEF DESCRIPTION OF THE DRAWINGS

The accompanying drawings, which are incorporated herein and form a part of the specification, illustrate the present invention and, together with the description, further serve to explain the principles of the invention and to enable a person skilled in the pertinent art to make and use the invention.

The present invention will be described with reference to the accompanying drawings. The drawing in which an element first appears is typically indicated by the leftmost digit(s) in the corresponding reference number.

DETAILED DESCRIPTION

While specific configurations and arrangements are discussed, it should be understood that this is done for illustrative purposes only. A person skilled in the pertinent art will recognize that other configurations and arrangements can be used without departing from the spirit and scope of the present invention. It will be apparent to a person skilled in the pertinent art that this invention can also be employed in a variety of other applications.

A. Implantable Medical Devices

Figure 1:
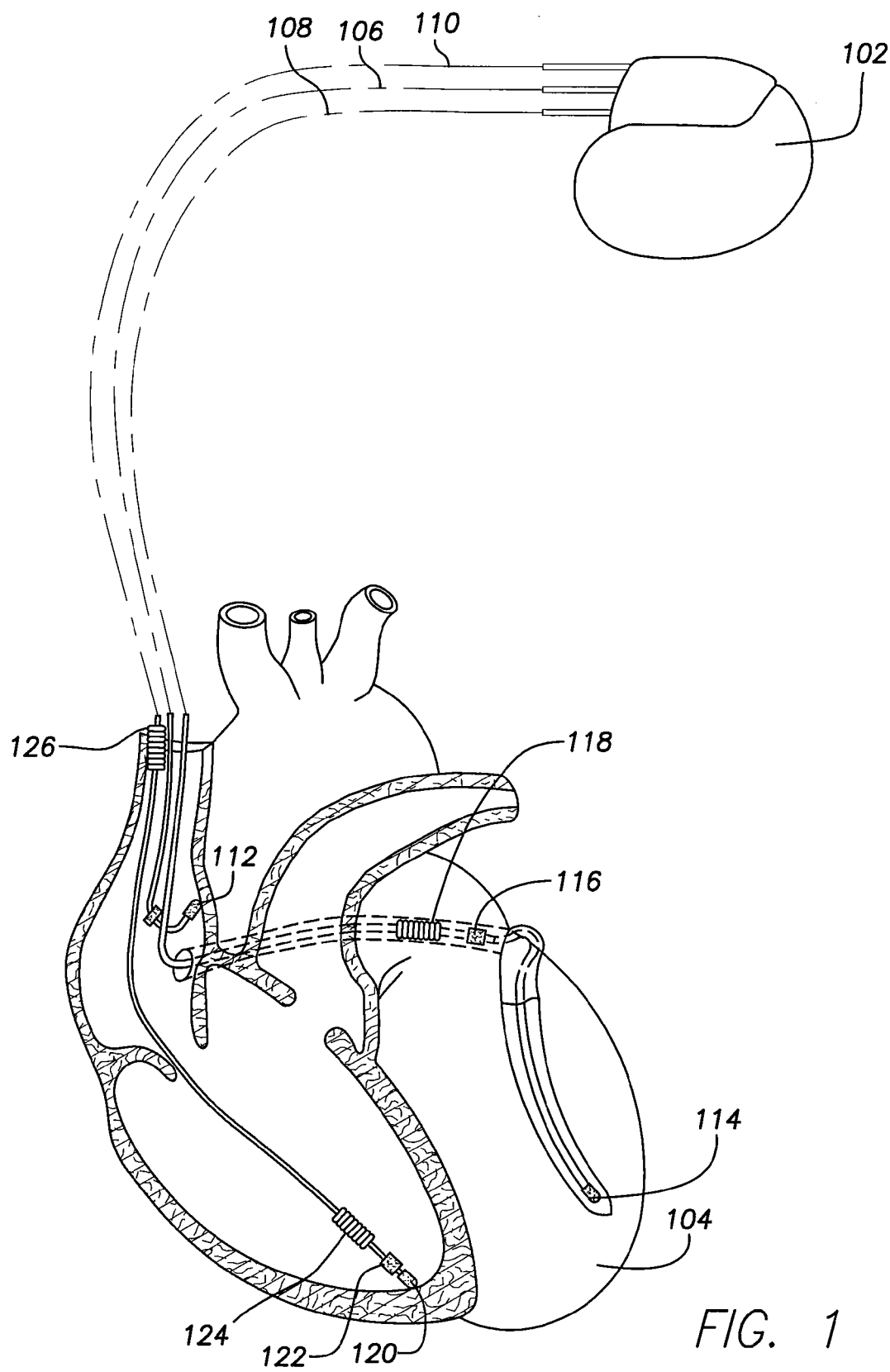
FIG. 1 is a diagram of an example implantable medical device ("IMD") used in the present invention.
Figure 2:
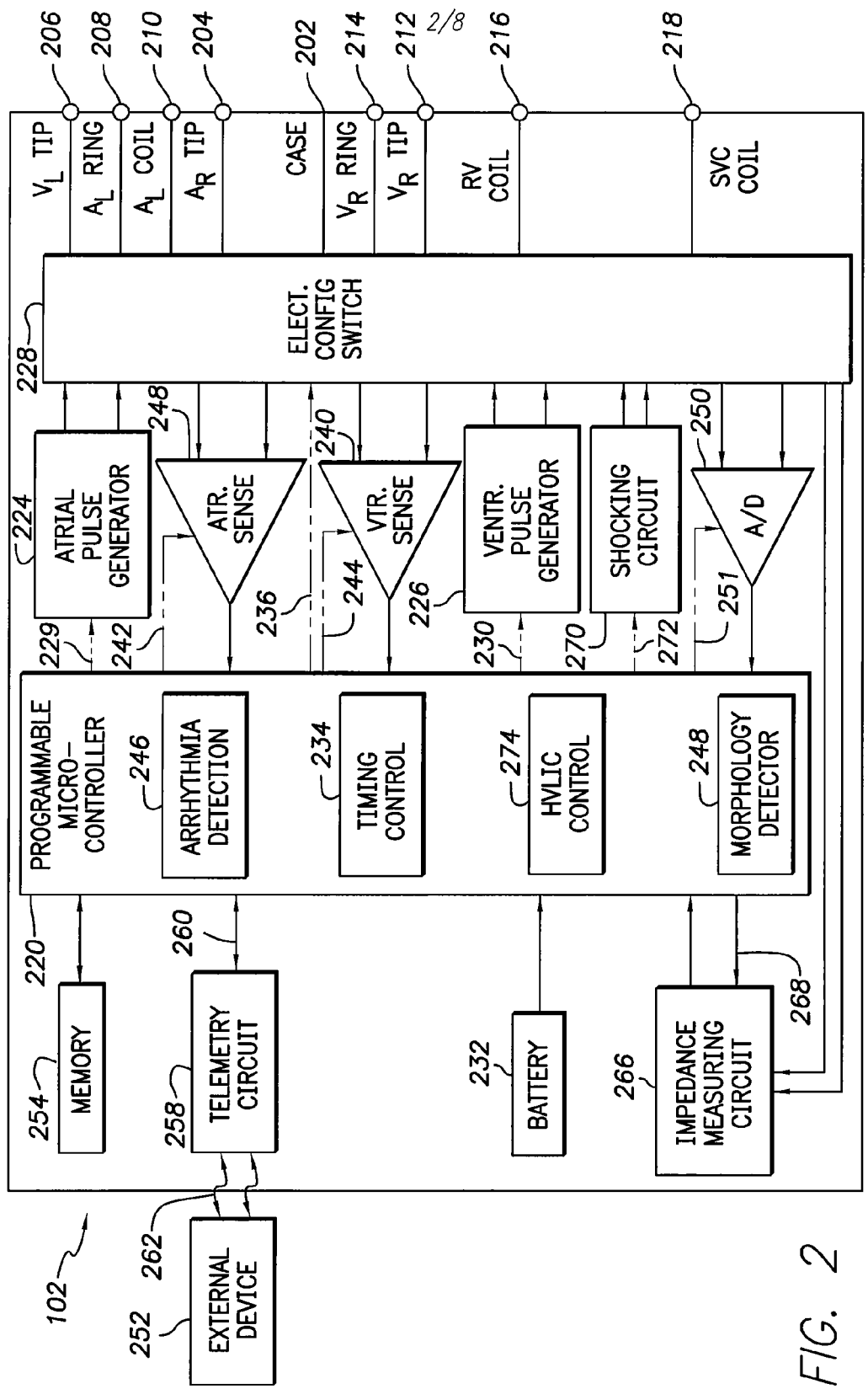
FIG. 2 is a block diagram of the example IMD of FIG. 1.

Implantable medical devices include, for example and without limitation, pacemakers, pulse generators, and cardioverter defibrillators. The term "implantable medical device," or simply "IMD," is used herein to refer to, non-exclusively and without limitation, any pacemaker, pulse generator, or cardioverter defibrillator. As used herein, the term IMD also includes other implantable devices such as artificial organs, insulin pumps, drug delivery devices, and other implanted devices for sensing physiologic parameters or delivering electrical or pharmaceutical therapy to the body. FIGS. 1 and 2 illustrate an example IMD environment.

As shown in FIG. 1, an exemplary IMD 102 is in electrical communication with a mammalian patient's heart 104 by way of three leads, 106, 108 and 110, suitable for delivering multi-chamber stimulation and pacing therapy. To sense atrial cardiac signals and to provide right atrial chamber stimulation therapy, IMD 102 is coupled to implantable right atrial lead 106 having at least an atrial tip electrode 112, which typically is implanted in the patient's right atrial appendage.

To sense left atrial and ventricular cardiac signals and to provide left-chamber pacing therapy, IMD 102 is coupled to "coronary sinus" lead 108 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, exemplary coronary sinus lead 108 is designed to receive atrial and ventricular cardiac signals and to deliver left ventricular pacing therapy using at least a left ventricular tip electrode 114, left atrial pacing therapy using at least a left atrial ring electrode 116, and shocking therapy using at least a left atrial coil electrode 118.

IMD 102 is also shown in electrical communication with the patient's heart 104 by way of an implantable right ventricular lead 110 having a right ventricular ("RV") tip electrode 120, a RV ring electrode 122, a RV coil electrode 124, and a superior vena cava ("SVC") coil electrode 126. Typically, right ventricular lead 110 is transvenously inserted into heart 104 so as to place the RV tip electrode 120 in the right ventricular apex so that RV coil electrode 124 will be positioned in the right ventricle and SVC coil electrode 126 will be positioned in the superior vena cava. Accordingly, right ventricular lead 110 is capable of receiving cardiac signals and delivering stimulation in the form of pacing and shock therapy to the right ventricle.

FIG. 2 shows a simplified block diagram of IMD 102, which is capable of treating both fast and slow arrhythmias with stimulation therapy, including cardioversion, defibrillation, and pacing stimulation. While a particular multi-chamber device is shown, it is shown for illustration purposes only, and one of skill in the art could readily duplicate, eliminate or disable the appropriate circuitry in any desired combination to provide a device capable of treating the appropriate chamber(s) with the desired cardioversion, defibrillation and pacing stimulation.

IMD 102 is shown schematically in FIG. 2. Housing 202 is often referred to as the "can," "case" or "case electrode" and may be programmed to act as the return electrode for all "unipolar" modes. Housing 202 is typically hermetically sealed. Housing 202 may further be used as a return electrode alone or in combination with one or more of coil electrodes 118, 124, and 126 for shocking purposes. Housing 202 further includes a connector (not shown) having a plurality of terminals, 204, 206, 208, 210, 212, 214, 216, and 218 (shown schematically and, for convenience, the names of the electrodes to which they are connected are shown next to the terminals). As such, to achieve right atrial sensing and pacing, the connector includes at least a right atrial tip terminal ($A_R$ TIP) 204 adapted for connection to atrial tip electrode 112.

To achieve left chamber sensing, pacing and shocking, the connector includes at least a left ventricular tip terminal ($V_L$ TIP) 206, a left atrial ring terminal ($A_L$ RING) 208, and a left atrial shocking terminal ($A_L$ COIL) 210, which are adapted for connection to left ventricular ring electrode 114, left atrial tip electrode 116, and left atrial coil electrode 118, respectively.

To support right chamber sensing, pacing, and shocking the connector also includes a right ventricular tip terminal ($V_R$ TIP) 212, a right ventricular ring terminal ($V_R$ RING) 214, a right ventricular shocking terminal (RV COIL) 216, and an SVC shocking terminal (SVC COIL) 218, which are configured for connection to RV tip electrode 120, RV ring electrode 122, RV coil electrode 124, and SVC coil electrode 126, respectively.

At the core of IMD 102 is a programmable microcontroller 220 which controls the various modes of stimulation therapy. As is well known in the art, microcontroller 220 typically includes a microprocessor, or equivalent control circuitry, designed specifically for controlling the delivery of stimulation therapy and can further include RAM or ROM memory, logic and timing circuitry, state machine circuitry, and I/O circuitry. Typically, microcontroller 220 includes the ability to process or monitor input signals (data) as controlled by a program code stored in a designated block of memory. The details of the design of microcontroller 220 are not critical to the present invention. Rather, any suitable microcontroller 220 can be used to carry out the functions described herein. The use of microprocessor-based control circuits for performing timing and data analysis functions are well known in the art.

Representative types of control circuitry that may be used with the invention include the microprocessor-based control system of U.S. Pat. No. 4,940,052 (Mann et al.) and the state-machines of U.S. Pat. Nos. 4,712,555 (Thornander et al.) and 4,944,298 (Sholder). For a more detailed description of the various timing intervals used within the IMD's and their inter-relationship, see U.S. Pat. No. 4,788,980 (Mann et al.). The '052, '555, '298 and '980 patents are incorporated herein by reference.

As shown in FIG. 2, an atrial pulse generator 224 and a ventricular pulse generator 226 generate pacing stimulation pulses for delivery by right atrial lead 106, right ventricular lead 110, and/or coronary sinus lead 108 via an electrode configuration switch 228. It is understood that in order to provide stimulation therapy in each of the four chambers of the heart, atrial and ventricular pulse generators 224 and 226 may include dedicated, independent pulse generators, multiplexed pulse generators, or shared pulse generators. Pulse generators 224 and 226 are controlled by microcontroller 220 via appropriate control signals 229 and 230, respectively, to trigger or inhibit the stimulation pulses. Power for the microcontroller 220, as well as for the various pulse generators, is supplied by a battery 232.

Microcontroller 220 further includes timing control circuitry 234 which is used to control pacing parameters (e.g., the timing of stimulation pulses) as well as to keep track of the timing of refractory periods, postventricular refractory period ("PVARP") intervals, noise detection windows, evoked response windows, alert intervals, marker channel timing, etc., which are well known in the art. Examples of pacing parameters include, but are not limited to, atrio-ventricular (AV) delay, interventricular (RV-LV) interval, interatrial (RA-LA) interval, and pacing rate.

Switch 228 includes a plurality of switches for connecting the desired electrodes to the appropriate I/O circuits, thereby providing complete electrode programmability. Accordingly, switch 228, in response to a control signal 236 from microcontroller 220, determines the polarity of the stimulation pulses (e.g., unipolar, bipolar, combipolar, etc.) by selectively closing the appropriate combination of switches (not shown) as is known in the art.

Atrial sensing circuit 238 and ventricular sensing circuit 240 may also be selectively coupled to right atrial lead 106, coronary sinus lead 108, and right ventricular lead 110 through switch 228 for detecting the presence of cardiac activity in each of the four chambers of the heart. Accordingly, the atrial (ATR. SENSE) and ventricular (VTR. SENSE) sensing circuits 238 and 240 may include dedicated sense amplifiers, multiplexed amplifiers, or shared amplifiers. Switch 228 determines the "sensing polarity" of the cardiac signal by selectively closing the appropriate switches, as is also known in the art. In this way, a clinician may program the sensing polarity independent of the stimulation polarity.

Each sensing circuit 238 and 240 preferably employs one or more low power precision amplifiers with programmable gain and/or automatic gain control, bandpass filtering, and a threshold detection circuit, as known in the art, to selectively sense the cardiac signal of interest. The automatic gain control enables IMD 102 to deal effectively with the difficult problem of sensing the low amplitude signal characteristics of atrial or ventricular fibrillation.

The outputs of atrial and ventricular sensing circuits 238 and 240 are connected to microcontroller 220 which, in turn, is able to trigger or inhibit atrial and ventricular pulse generators, 224 and 226, respectively, in a demand fashion in response to the absence or presence of cardiac activity, in the appropriate chambers of the heart. Sensing circuits 238 and 240, in turn, receive control signals over signal lines 242 and 244 from microcontroller 220 for purposes of measuring cardiac performance at appropriate times, and for controlling the gain, threshold, polarization charge removal circuitry (not shown), and timing of any blocking circuitry (not shown) coupled to the inputs of sensing circuits 238 and 240.

For arrhythmia detection, IMD 102 utilizes the atrial and ventricular sensing circuits 238 and 240 to sense cardiac signals to determine whether a rhythm is physiologic or pathologic. The timing intervals between sensed events (e.g., P-waves, R-waves) are then classified by microcontroller 220 by comparing them to a predefined rate zone limit (e.g., bradycardia, normal, low rate VT, high rate VT, and fibrillation rate zones) and various other characteristics (e.g., sudden onset, stability, physiologic sensors, morphology, etc.) in order to determine the type of remedial therapy that is needed (e.g., bradycardia pacing, anti-tachycardia pacing, cardioversion shocks or defibrillation shocks, collectively referred to as "tiered therapy"). According to the present invention, blood pressure analysis provides an additional source of information for optimization of IMD performance for arrhythmia therapy.

Microcontroller 220 utilizes arrhythmia detection circuitry 246 and morphology detection circuitry 248 to recognize and classify arrhythmias so that appropriate therapy can be delivered. Microcontroller 220 further includes a high-voltage lead impedance check ("HVLIC") control 274 for checking and calibrating the impedance of the high-voltage leads coupled to IMD 102.

Cardiac signals are also applied to the inputs of an analog-to-digital (A/D) data acquisition system 250. Data acquisition system 250 is configured to acquire intracardiac electrogram signals, convert the raw analog data into a digital signal, and store the digital signals for later processing and/or telemetric transmission to an external device 252. In the present invention, external device 252 may be an implantable RF telemetry module. Data acquisition system 250 is coupled to right atrial lead 106, coronary sinus lead 108, and right ventricular lead 110 through switch 228 to sample cardiac signals across any pair of desired electrodes.

Data acquisition system 250 can be coupled to microcontroller 220, or other detection circuitry, for detecting an evoked response from heart 104 in response to an applied stimulus, thereby aiding in the detection of "capture." Capture occurs when an electrical stimulus applied to the heart is of sufficient energy to depolarize the cardiac tissue, thereby causing the heart muscle to contract. Microcontroller 220 detects a depolarization signal during a window following a stimulation pulse, the presence of which indicates that capture has occurred. Microcontroller 220 enables capture detection by triggering ventricular pulse generator 226 to generate a stimulation pulse, starting a capture detection window using timing control circuitry 234 within microcontroller 220, and enabling data acquisition system 250 via control signal 251 to sample the cardiac signal that falls in the capture detection window and, based on the amplitude, determines if capture has occurred.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et al.); and U.S. Pat. No. 5,350,410 (Kleks et al.), which patents are hereby incorporated herein by reference. The type of capture detection system used is not critical to the present invention.

Microcontroller 220 is further coupled to a memory 254 by a suitable data/address bus 256, wherein the programmable operating parameters used by microcontroller 220 are stored and modified, as required, in order to customize the operation of IMD 102 to suit the needs of a particular patient. Such operating parameters define, for example, pacing pulse amplitude, pulse duration, electrode polarity, rate, sensitivity, automatic features, arrhythmia detection criteria, and the amplitude, waveform shape and vector of each shocking pulse to be delivered to the patient's heart 104 within each respective tier of therapy.

The operating parameters of IMD 102 may be non-invasively programmed into memory 254 through a telemetry circuit 258 in telemetric communication with external device 252, such as a programmer, transtelephonic transceiver, or a diagnostic system analyzer. Telemetry circuit 258 is activated by microcontroller 220 by a control signal 260. Telemetry circuit 258 allows intracardiac electrograms and status information relating to the operation of IMD 102 (as contained in microcontroller 220 or memory 254) to be sent to external device 252 through an established communication link 262. As will be discussed in more detail below, telemetry circuit 258 may be a magnetic telemetry coil transmitting to an implanted RF transmitter, which will further relay a signal to another external device.

For examples of IMDs, see U.S. Pat. No. 4,809,697, entitled "Interactive Programming and Diagnostic System for use with Implantable Pacemaker" (Causey, Ill. et al.); U.S. Pat. No. 4,944,299, entitled "High Speed Digital Telemetry System for Implantable Device" (Silvian); and U.S. Pat. No. 6,275,734, entitled "Efficient Generation of Sensing Signals in an Implantable Medical Device such as a Pacemaker or ICD" (McClure et al.), which patents are hereby incorporated herein by reference.

Telemetry circuit 258 also allows optimization parameters obtained externally to be sent into microcontroller 220. Data may be assessed by a physician during a patient visit and, on the direction of the physician, could be transmitted to microcontroller 220 for analysis and optimization of a number of parameters, as discussed below. Analysis may also be completed externally at a physician's office with instructions based on the analysis transmitted to microcontroller 220. The instructions may be transmitted from an external device in, for example, the physician's office, to an implanted RF transmitter which then relays the instructions to IMD 102. Alternatively, the instructions may be transmitted directly to IMD 102 through magnetic telemetry circuit 258.

IMD 102 further includes a magnet detection circuitry (not shown), coupled to microcontroller 220. It is the purpose of the magnet detection circuitry to detect when a magnet is placed over IMD 102, which magnet may be used by a clinician to perform various test functions of IMD 102 and/or to signal microcontroller 220 that the external programmer 252 is in place to receive or transmit data from or to microcontroller 220 directly or indirectly through telemetry circuit 258.

As further shown in FIG. 2, IMD 102 includes an impedance measuring circuit 266 which is enabled by microcontroller 220 via a control signal 268. The known uses for an impedance measuring circuit 266 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 266 is advantageously coupled to switch 228 so that any desired electrode may be used.

In the case where IMD 102 is intended to operate as a cardioverter, pacer or defibrillator, it must detect the occurrence of an arrhythmia and automatically apply an appropriate electrical therapy to the heart aimed at terminating the detected arrhythmia. To this end, microcontroller 220 further controls a shocking circuit 270 by way of a control signal 272. The shocking circuit 270 generates shocking pulses of low (up to 0.5 Joules), moderate (0.5-10 Joules), or high energy (11 to 40 Joules), as controlled by microcontroller 220. Such shocking pulses are applied to the patient's heart 104 through at least two shocking electrodes (e.g., selected from left atrial coil electrode 118, RV coil electrode 124, and SVC coil electrode 126). As noted above, housing 202 may act as an active electrode in combination with RV electrode 124, or as part of a split electrical vector using SVC coil electrode 126 or left atrial coil electrode 118 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 Joules), delivered asynchronously (since R-waves may be too disorganized to be recognize), and pertaining exclusively to the treatment of fibrillation. Accordingly, microcontroller 220 is capable of controlling the synchronous or asynchronous delivery of the shocking pulses.

B. H-Bridge

Figure 9:
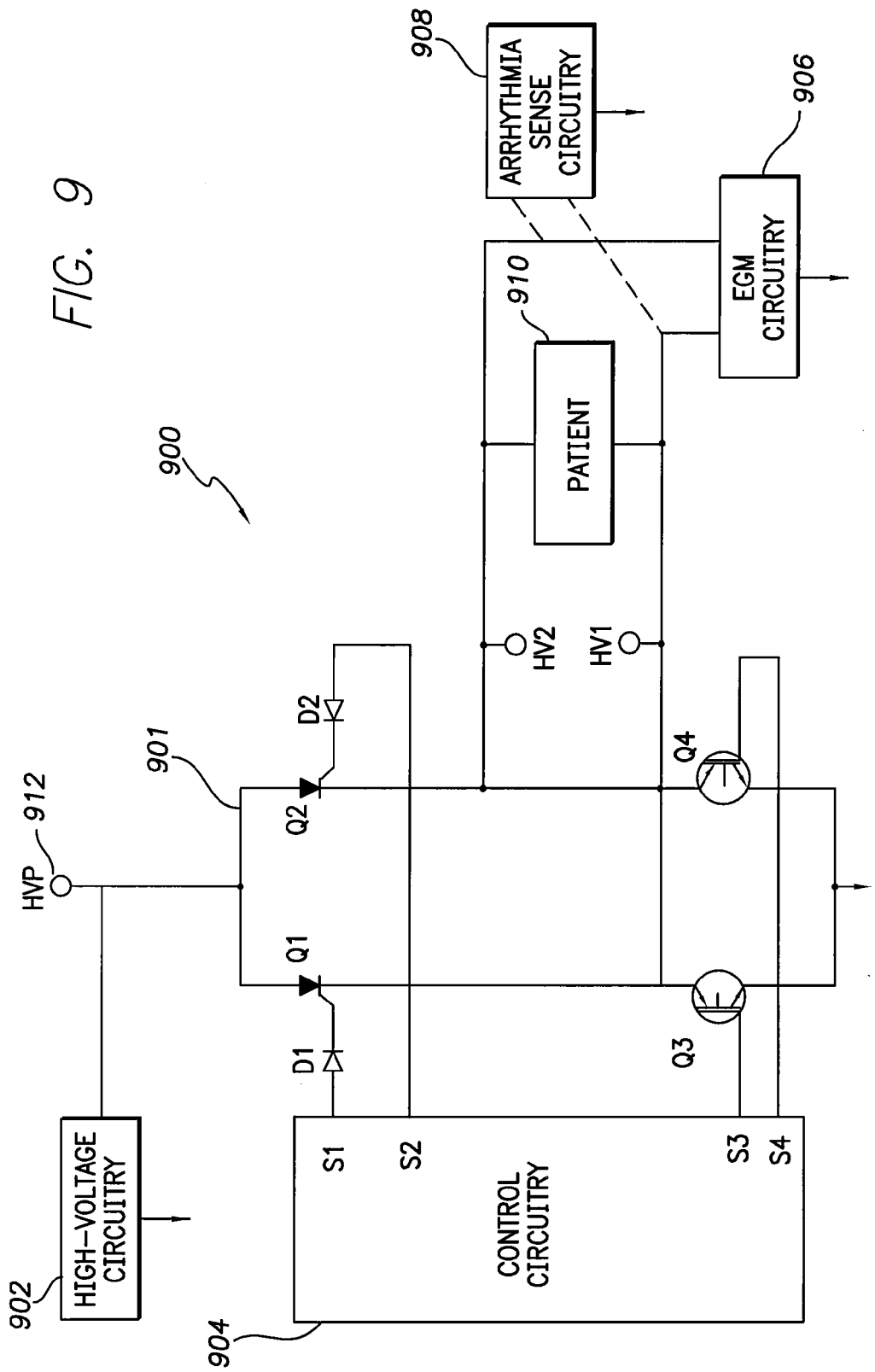
FIG. 9 is an illustration of a high-voltage circuit that may be used in the present invention.

FIG. 9 shows a combination schematic and block diagram of an example high-voltage output circuit 900. Circuit 900 includes an H-bridge 901, high-voltage circuitry 902, control circuitry 904, electrogram ("EGM") circuitry 906, and arrhythmia sense circuitry 908. H-bridge 901 includes thyristors Q1 and Q2, diodes D1 and D2, and insulating gate bipolar transistors ("IGBT") Q3 and Q4. Thyristors Q1 and Q2 may be, for example, silicon controlled rectifiers ("SCR") or triacs.

Thyristors Q1 and Q2 may replace the upper bridge IGBTs found in some IMDs. Diodes D1 and D2 are isolating diodes into the gates of thyristors Q1 and Q2, respectively, and block current from flowing from thyristors Q1 and Q2 back into the IMD. Q3 and Q4 are IGBTs. This design is valid for a ground-referenced output stage where the high and low voltage sections are referenced to the same ground. High voltage circuitry 902 includes high-voltage capacitors and associated charging circuitry. This may include a fly-back transformer and associated circuitry. High voltage circuitry 902 may convert a high-voltage capacitor pair from a parallel to a series configuration.

Control circuitry 904 includes components needed to generate the drive signals for switching the bridge components. As will be discussed, the trigger current for thyristors Q1 and Q2 may be on the order of 40 mA for a very short duration, such as on the order of tens of microseconds. Both thyristors Q1 and Q2 and IGBTs Q3 and Q4 may need, for example, a 10 V to 15 V ground-referenced current drive.

EGM circuitry 906 may include circuitry to sense the electrogram on the shocking leads of the IMD. EGM circuitry 906 includes a differential amplifier with very high input impedance with protection circuitry that limits in-rush current and/or excess voltage to the amplifier.

Arrhythmia sense circuitry 908 is indirectly coupled to a patient 910 through the low voltage sense leads on the IMD. This path is only available in situ. Current into arrhythmia sense circuitry 908 may be limited when a defibrillation shock is performed. For example, current into arrhythmia sense circuitry 908 may be limited to less than 5 mA when an 800 V defibrillation shock is performed.

For an example H-bridge circuit used in an IMD, see U.S. Pat. No. 5,833,712, entitled "Implantable Defibrillator System for Generating a Biphasic Waveform" (Kroll et al.).

C. HVLIC

Low voltage pulses may be used to determine the impedance of the high-voltage leads connected to the IMD. By maintaining a sufficiently low voltage and current, a painless HVLIC can be performed.

Figure 3:
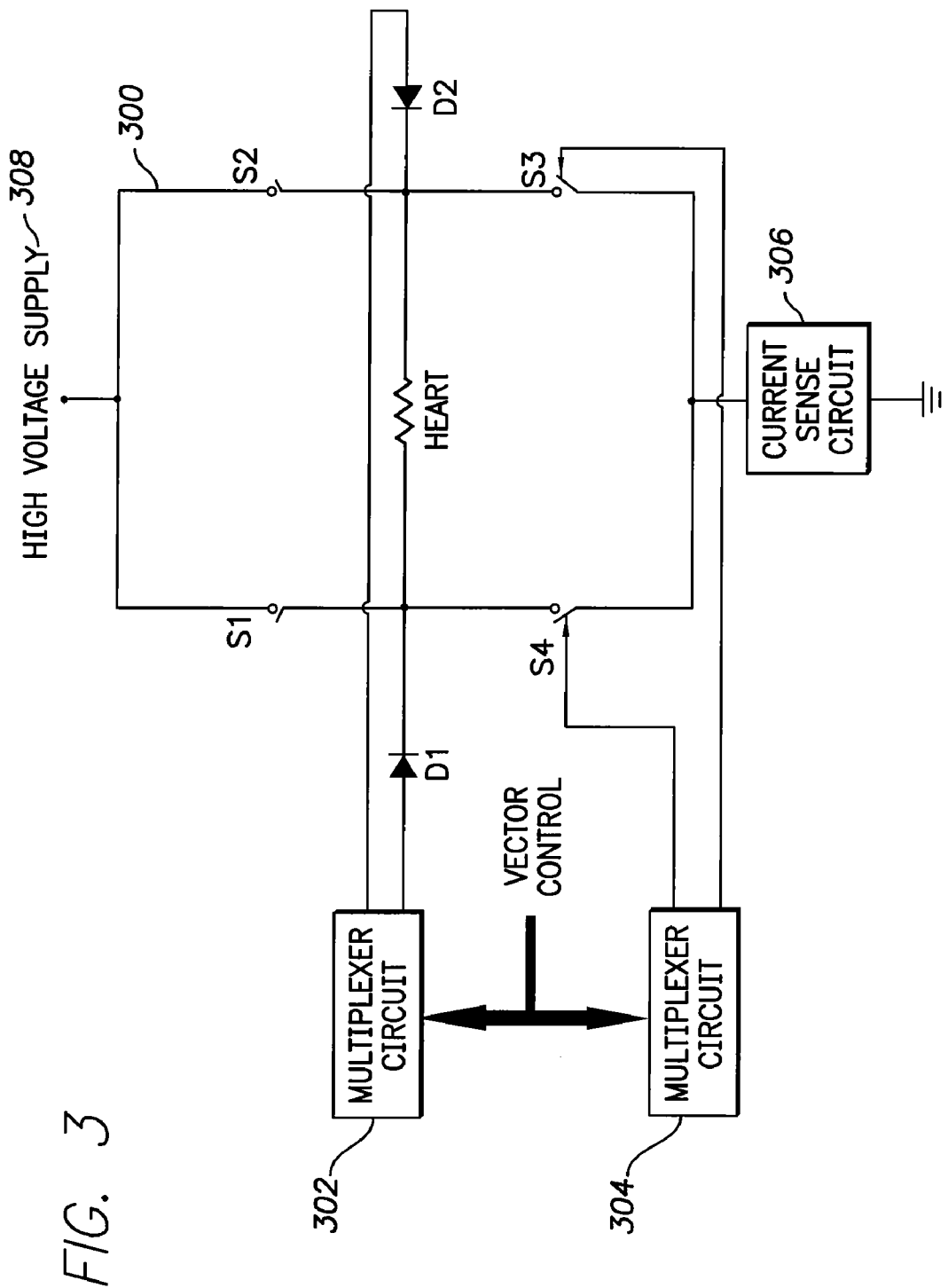
FIG. 3 is a block diagram of a high voltage circuit for use in an IMD.

Another embodiment is to use existing H-bridge circuitry of the IMD, such as that described above, but add a diode with the cathode connected to the point between switches, which may be Insulated Gate Bipolar Transistors ("IGBTs") or thyristors, in any or all half-bridges. The anode of the diode may be connected to the constant current or voltage circuitry. FIG. 3 is an illustration of a 2-legged H-bridge 300 having such a connection. Similarly to H-bridge 901 described with respect to FIG. 9, H-bridge 300 includes upper bridge switches S1 and S2, lower bridge switches S3 and S4, and diodes D1 and D2. Diode D1 is coupled to H-bridge 300 between switches S1 and S4, and diode D2 is coupled to H-bridge 300 between switches S2 and S3. Multiplexer circuits 302 and 304 are used to direct current and voltage through diodes D1 and D2 to the proper switches to measure the impedance across desired leads. Current sense circuit 306 is coupled to H-bridge 300 between switches S3 and S4, and senses current delivered through the lead. High voltage supply 308 is coupled to H-bridge 300 at switches S1 and S2.

A separate voltage or current source may be required to perform the HVLIC measurement. Alternatively, the existing source can be used to supply the switching components in the H-bridge without requiring extra connections to be made to the patient.

i. Constant Current

Figure 4:
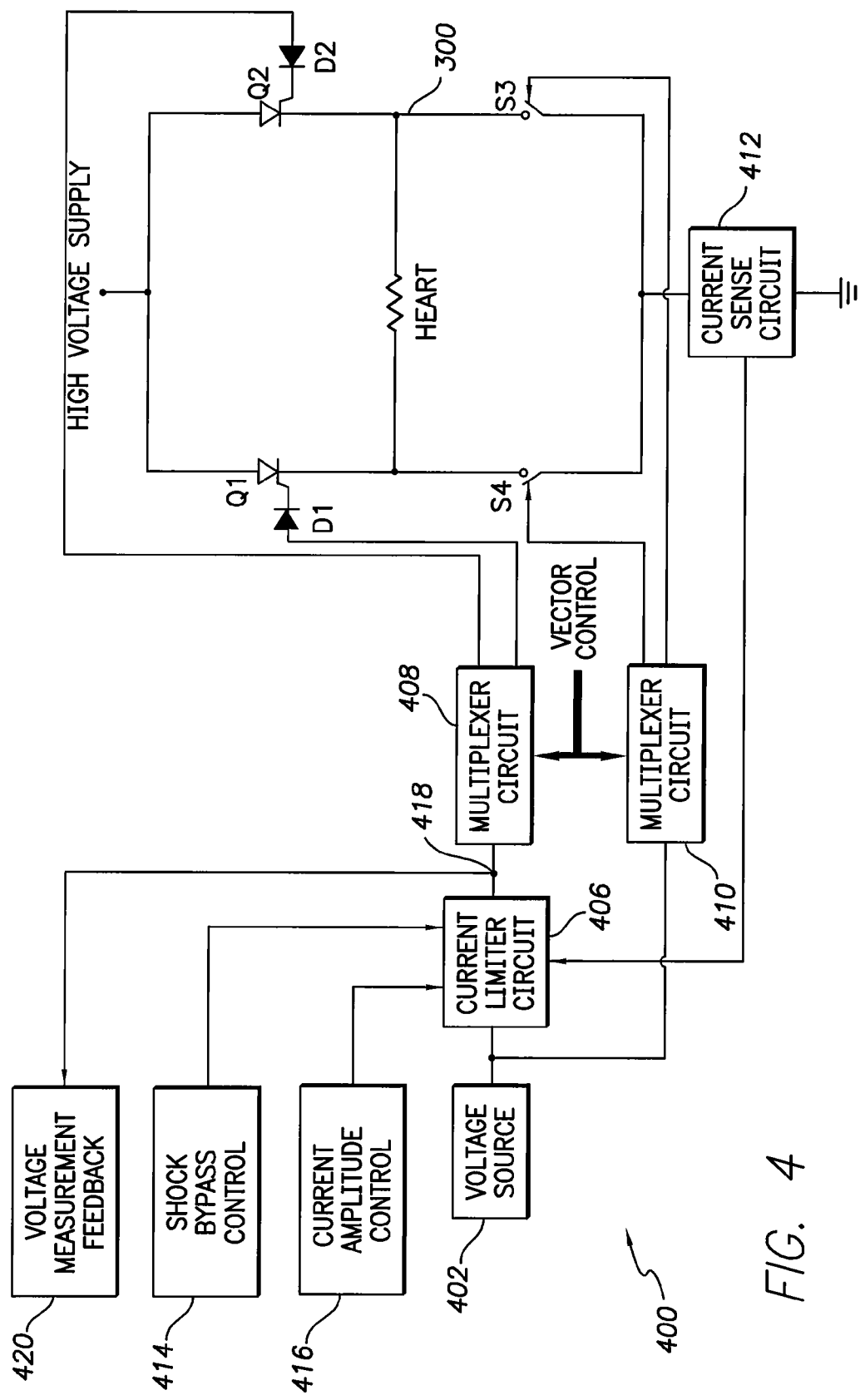
FIG. 4 is a block diagram of a high voltage circuit for use with a constant current method of determining impedance.

FIG. 4 shows a circuit 400 for use with an HVLIC constant current method, in which constant current is injected through the high-side switching component to determine the impedance. Voltage source 402 is capable of supplying adequate current for lead impedance measurement. Voltage source 402 may also be used to trigger switches in a high-voltage bridge of the IMD, such as H-bridge 300. A current limiting circuit 406 is used to source a programmable current into thyristors Q1 and Q2, which are the upper bridge switches. Multiplexer circuits 408 and 410 are used to direct the current and voltage to the proper switches to measure the impedance across the desired leads.

In the embodiment of FIG. 4, voltage source 402 turns on the lower component of bridge 300 through multiplexer 410. Voltage source 402 also sources the current for the HVLIC procedure. Current limiter circuit 406 receives input from a current sense circuit 412, which senses the current delivered through the lead. Current sense circuit 412 can be substituted by circuitry within the source 402 or the limiter 406 or the multiplexer 408. This feedback is used to control the amount of current delivered. Current limiter 406 also has a bypass control 414 such that full current is used to turn thyristors Q1 and Q2 on during a defibrillation shock. Current limiter circuit 406 may also have a current amplitude control 416 that sets the amount of desired current to be used.

The voltage is measured at node 418, relative to ground, using voltage measurement feedback circuitry 420, regardless of which lead is measured. Voltage drops across multiplexer circuits 408 and 410, diodes D1 and D2, thyristors Q1 and Q2, IGBTs S3 and S4, and current sense circuit 412 can be characterized and subtracted from the measured voltage. The measured voltage and the known current can then be used to determine the lead impedance.

The sourced current can be on the order of tens of milliamperes. This will induce a small voltage in the heart which will not typically be felt by the patient. Additionally, feedback may be used to determine whether the HVLIC pulse captured the cardiac tissue. If so, the amplitude of the HVLIC current pulse can be lowered. If the sourced current is sufficiently small, such as, for example, less than 0.5 $I_T$ (trigger current for a thyristor), the measurement can be performed with the high-voltage capacitors charged. Otherwise, high voltage should not be present.

Figure 5:
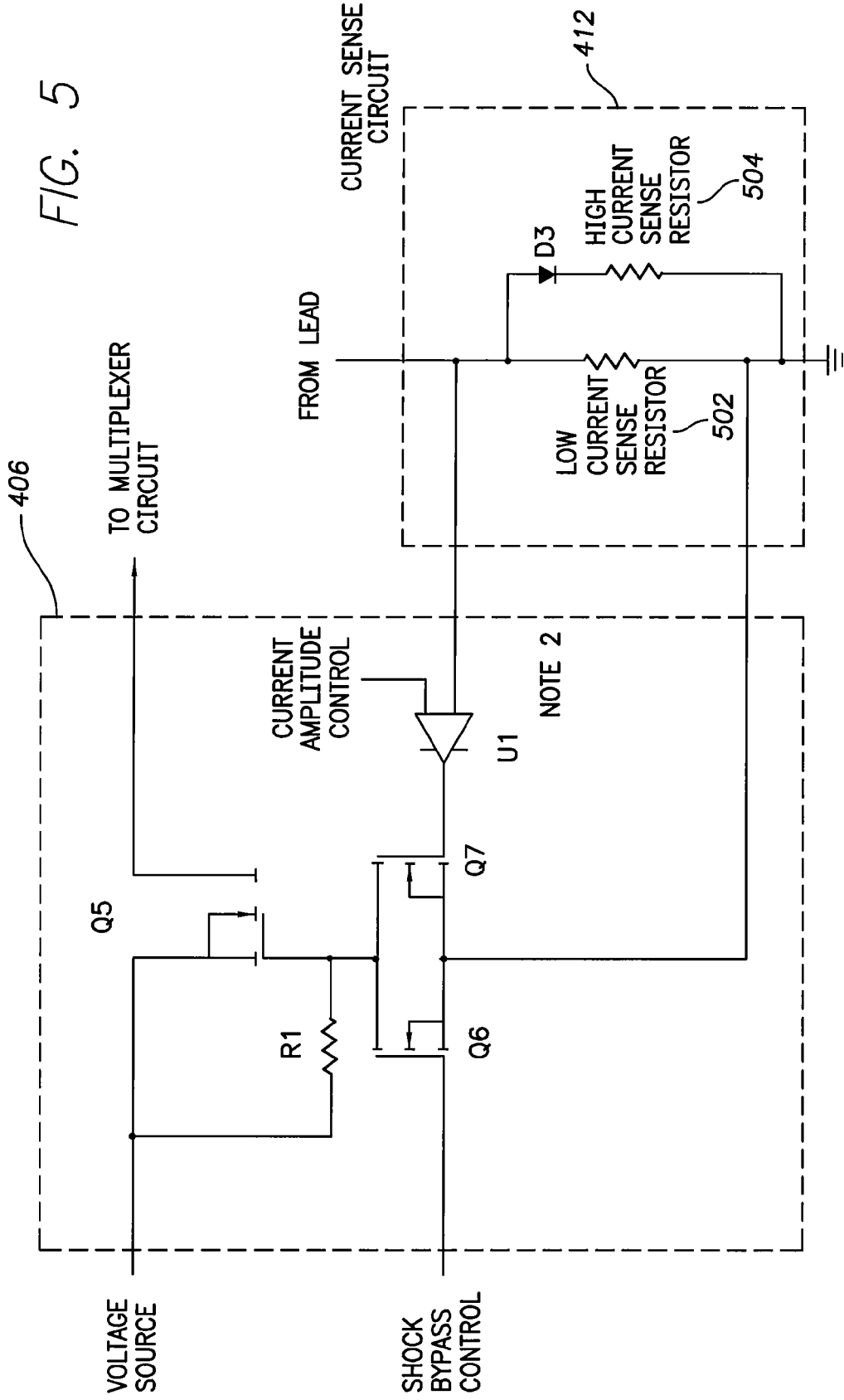
FIG. 5 is a block diagram of a current limiter circuit and a current sense circuit for use with a high voltage circuit.

FIG. 5 is an example embodiment of current limiter circuit 406 and current sense circuit 412. Current sense circuit 412 utilizes two resistors to sense the current. Low current sense resistor 502 may be relatively large in value and used to sense currents in the milliampere range. If the current is large enough, diode D3 conducts and high current sense resistor 504 is used to measure the defibrillation current. High current sense resistor 504 is thus a much smaller resistor. Current limiter circuit 406 is set to a specific current determined by current amplitude control at comparator U1. Transistor Q7 is used to control transistor Q5, which regulates the current delivered. Transistor Q6 is used to fully turn on transistor Q5 in the event of a defibrillation shock.

ii. Constant Voltage

Figure 6:
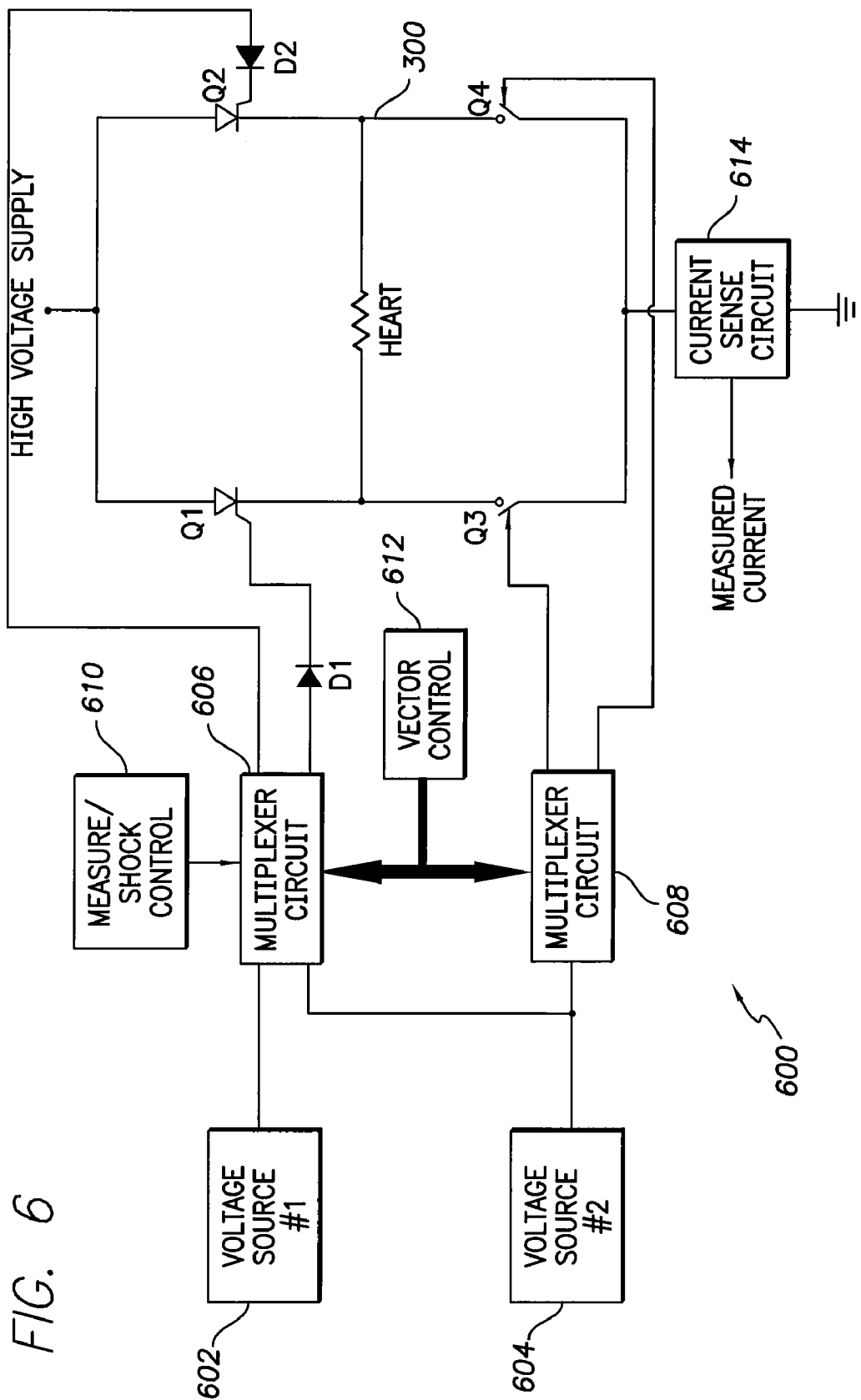
FIG. 6 is a block diagram of a high voltage circuit for use with a constant voltage method of determining impedance.

FIG. 6 shows a block diagram of a circuit 600 for use with an HVLIC constant voltage method, in which constant voltage is applied to the gate of the high-side thyristor to determine the impedance. Circuit 600 may include a first voltage source 602 and a second voltage source 604. Second voltage source 604 may be a known voltage source, and may be used to supply an unknown current to the leads. Second voltage source 604 may also be used in an IMD to supply voltage to other devices in the IMD for different purposes. First voltage source 602 may be a higher voltage source that is used to switch the devices during a high-voltage shock. One of skill in the art will recognize that two separate voltage sources are not required, although they may be desirable. Multiplexer circuits 606 and 608 route the voltage to the proper switch. For HVLIC, first voltage source 602 is routed to thyristor Q1 or Q2, using a measure/shock control 610 and vector control 612. Second voltage source 604 is routed to IGBTs Q3 or Q4 using vector control 612. Current is measured from current sense circuit 614 in a similar manner to that described for current sense circuit 412. Alternatively, the current measurement may be made at source 602 or anywhere within the loop. The known voltage and measured current can then be used to determine lead impedance.

iii. Calibration

Inaccuracies in measuring the lead impedance can come from the voltage drops in the measurement path, as well as part to part variations. For example, the voltage induced across the lead may be 0.5V, while the voltage drops across the diode and the gate of the SCR, for example, may be 0.7V each. The added voltage drops must be subtracted from the measured voltage since they constitute most of the measured voltage.

Both the constant current and constant voltage methods presented above allow for self-calibration of the HVLIC circuitry. Because the currents and voltages are relatively small, short circuiting one leg of H-bridge 300 is possible, provided there is no high voltage ("HV") present. By doing this, the voltage drop across the current path can be measured with no lead attached. Switches S4 and S3 have very similar voltage drops.

Figure 7:
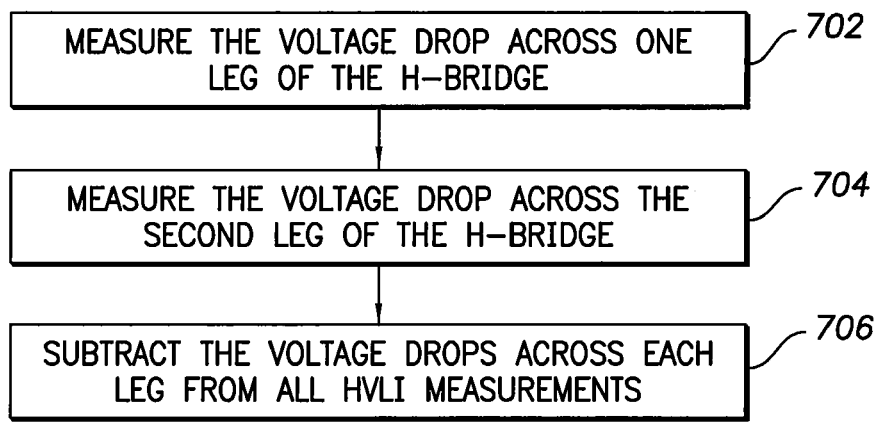
FIG. 7 is a flowchart of a calibration method.

FIG. 7 is a flowchart of a calibration method 700 according to an embodiment of the present invention. In step 702, the voltage drop across one leg of the H-bridge is measured. This may be accomplished by turning on one of the lower IGBTs in the H-bridge, such as IGBT Q3, to inject current through the diode and thyristor on the same side of the H-bridge. In this example, the diode and thyristor on the same side of the H-bridge as IGBT Q3 are diode D1 and thyristor Q1. The resulting voltage represents the drop across all elements of the loop, such as the multiplexer, diode D1, thyristor Q1, and IGBT Q3. The IGBT is then turned off.

In step 704, the voltage drop across the other leg of the H-bridge is measured. Similarly to step 702, this may be accomplished by turning on the lower IGBT on the second leg of the H-bridge, which in this example is IGBT Q4, to inject current in the diode and thyristor on the same side of the H-bridge, which in this example are diode D2 and thyristor Q2. The resulting voltage represents the drop across all elements of the loop, such as the multiplexer, diode D2, thyristor Q2, and IGBT Q4.

In step 706, the voltage from step 702 and the voltage from step 704 can be averaged and only one calibration value need be stored, either as a voltage offset or as equivalent impedance. This calibration method thus requires no manual intervention or leads attached and can be checked anytime during the life of the IMD.

Figure 8:
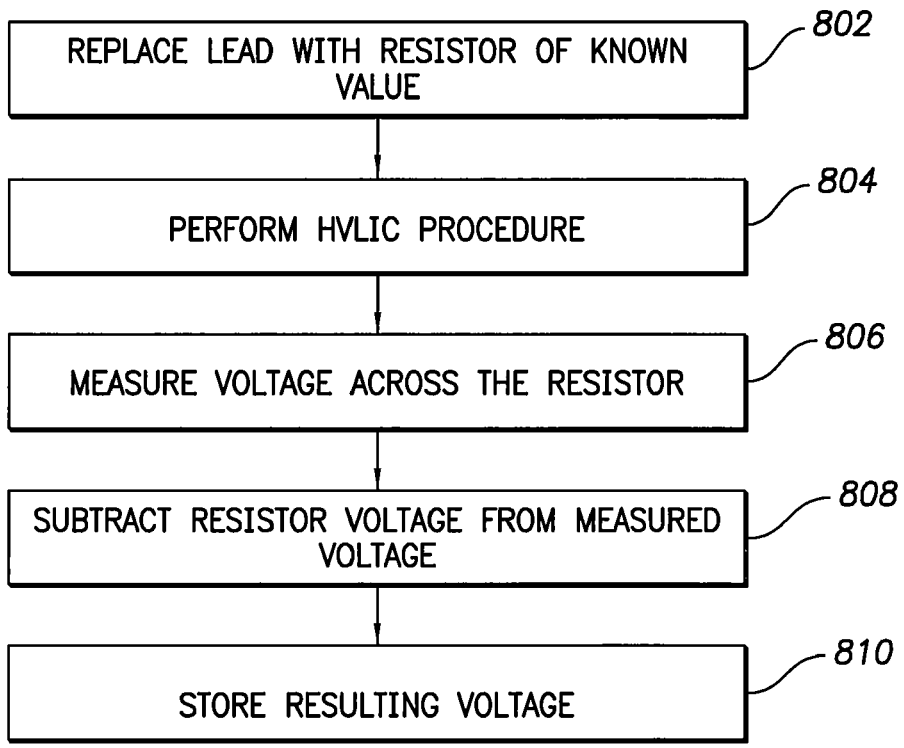
FIG. 8 is another flowchart of a calibration method.

Calibration of the device can also be performed using an external calibration tool, such as a resistor having a known value. FIG. 8 is a flowchart of a constant voltage calibration method 800 according to an embodiment of the present invention. In step 802, one of the leads of the IMD is replaced with a resistor having a known value. The lead ports can also simply be short-circuited. In this instance, a resistor of zero Ohms would be used.

In step 804, an HVLIC procedure is performed. In step 806, the voltage directly across the resistor is measured. In step 808, the known resistor voltage is subtracted from the voltage measured in step 806. In step 810, the resulting voltage is stored to be subtracted from all subsequent HVLI measurements.

Alternatively, typical voltage drops may be stored in the device and used to estimate the overall voltage drop in the measurement path. The overall error is then subtracted from all subsequent HVLI measurements.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

What is claimed is:

1. An apparatus for performing an impedance check of a high-voltage lead of an implantable medical device, said apparatus comprising:
a high-voltage bridge adapted to be coupled to a high-voltage capacitor and the high-voltage lead, the high-voltage bridge comprising a thyristor having a gate, an isolating diode coupled to the gate of the thyristor, and an insulated gate bipolar transistor (IGBT);
a multiplexer circuit coupled to the isolating diode and configured to route current through the isolating diode into the gate of the thyristor to perform an impedance check;
a current limiter circuit coupled to the multiplexer circuit and configured to control a flow of the current into the multiplexer circuit; and
a ground-referenced voltage source coupled to the current limiter circuit, the voltage source configured to provide triggering signals for the isolating diode and the IGBT and to provide current for performance of the impedance check.

2. The apparatus of claim 1, further comprising:
a shock bypass control coupled to the current limiter circuit and configured to remove limitations on current when a defibrillation shock is required so that the current to the gate is sufficient to turn on the thyristor.

3. The apparatus of claim 1, wherein the current limiter circuit is configured to limit the amount of current provided to perform the lead impedance check to less than that required to turn on the thyristor.

4. The apparatus of claim 1, further comprising a current amplitude control coupled to the current limiter circuit.

5. The apparatus of claim 1 wherein the thyristor has an associated trigger current and, if the current to perform the impedance check is less than the trigger current, then the impedance check may be performed with the high-voltage capacitor charged.

6. The apparatus of claim 1 wherein the thyristor has an associated trigger current and, if the current to perform the impedance check is at or above the trigger current, then the impedance check is performed with the high-voltage capacitor not charged.

7. The apparatus of claim 1 wherein the ground-referenced voltage is configured to provide triggering signals to the isolating diode and the IGBT through the multiplexer circuit.

8. The apparatus of claim 1 further comprising a current sense circuit coupled between the high-voltage bridge and the current limiter circuit, the current sense circuit configured to sense current delivered through the high-voltage lead during the impedance check and to provide an input to the current limiter circuit.

9. The apparatus of claim 8 wherein the current limiter circuit is configured to maintain the current used to perform an impedance check at a substantially constant amount based on the input received from the current sense circuit.

10. The apparatus of claim 8, wherein the current sense circuit comprises:
a low current sense resistor configured to sense currents in the milliampere range;
a high current sense resistor configured to sense a defibrillation current; and
a diode coupled between the low current sense resistor and the high current sense resistor and configured to conduct current above a high voltage lead impedance check level.

11. The apparatus of claim 10, wherein the current limiter circuit comprises:
a first transistor configured to control current delivered from the voltage source;
a second transistor configured to turn on the first transistor when a defibrillation shock is applied;
a third transistor configured to control the first transistor; and
a fourth transistor configured to bypass the third transistor.

12. The apparatus of claim 10, wherein the current limiter circuit comprises:
a first transistor configured to control current delivered from the voltage source;
a second transistor configured to turn on the first transistor when a defibrillation shock is applied;
a third transistor configured to control the first transistor; and
a comparator configured to control amplitude of the current by comparing a desired current with current delivered through the current sense circuit.

\* \* \* \* \*